United States Patent [19]

Baudet et al.

[11] 4,118,583

[45] Oct. 3, 1978

[54] MIXED ESTERS OF POLYOLS

[75] Inventors: Pierre Baudet, Genèva; Jean-Paul Ricard; Adrian Schulthess, both of Vaud, all of Switzerland

[73] Assignee: Laboratoires om Societe Anonyme, Geneva, Switzerland

[21] Appl. No.: 747,567

[22] Filed: Dec. 6, 1976

[30] Foreign Application Priority Data

Jan. 8, 1976 [CH] Switzerland ............................ 173/76
Jul. 30, 1976 [CH] Switzerland .......................... 9790/76

[51] Int. Cl.$^2$ ............................................ C07C 69/76
[52] U.S. Cl. ...................................................... 560/63
[58] Field of Search ...................... 260/473 G; 560/63

[56] References Cited

U.S. PATENT DOCUMENTS 3,494,957  2/1970  Nakanishi et al. ..................... 560/63

Primary Examiner—Paul J. Killos

Attorney, Agent, or Firm—Ladas, Parry, Von Gehr, Goldsmith & Deschamps

[57] ABSTRACT

Therapeutically active compounds of the general formula:

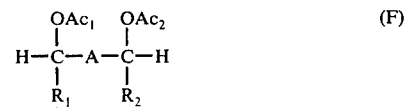

(F)

wherein $Ac_1$ is a first acyl group, $Ac_2$ is a second acyl group different from $Ac_1$, A is a C—C bond or a divalent organic residue; $R_1$, $R_2$ are a hydrogen atom or a lower alkyl group, $R_1$ and $R_2$ together being able to take part in the formation of a ring having up to 6 atoms, A, $R_1$ and $R_2$ may be substituted by —OH groups esterified or not by acyl groups.

7 Claims, No Drawings

MIXED ESTERS OF POLYOLS

This invention is directed to therapeutically active mixed esters of polyols having the general formula:

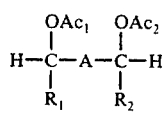

wherein $Ac_1$ is a first acyl group, $Ac_2$ is a second acyl group different from the first one, A is a C—C bond or a divalent acid residue; $R_1$, $R_2$ are a hydrogen atom or a lower alkyl group, $R_1$ and $R_2$ being able to form a ring of up to 6 atoms of A, $R_1$ and $R_2$ can be substituted by —OH groups substituted or unsubstituted by acyl groups.

The latter can be $Ac_1$ and/or $Ac_2$ groups, or other acyl groups, such as acetyl, nicotinyl, —$SO_3H$ or —$PO_3H_2$ groups.

Compounds of formula F contain one or more $Ac_1$ or $Ac_2$ groups.

The preferred $Ac_1$ residue is the 2-p-chloro-phenoxy-2-methylpropionyl or clofibril residue having the formula:

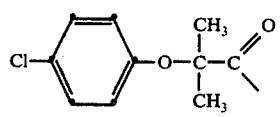

and the preferred $Ac_2$ residue is the acetylsalicyl residue of formula:

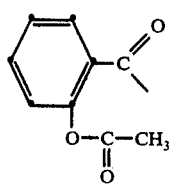

Compounds of formula F have pharmacological and clinical properties characterized by an hypolipemient, and hypocholesterolemient action, and which inhibits the aggregation of blood platelets. Said compounds can be compounded in pharmaceutical compositions and administered in various ways in the various pharmaceutical forms, e.g. orally, in the form of tablets or capsules.

The methods of synthesis of compounds of formula F are based on the introduction of acyl residues on polyalcohols having free or partially protected functions. The protective functions can be removed by acid hydrolysis, hydrogenolysis or directly transformed into esters by the acylating function. The choice of introduction of the acylating residues depends on the ratio desired between the different kinds of acylating functions.

The synthetic methods comprise:

(1) The introduction of one or more acyl residues of one kind onto symmetrical polyols, protecting the integrity of one or more alcohol functions which will be esterified by one or more acylating groups of another kind.

(2) The use of an alcohol protecting function such as a hydrolysable or hydrogenolysable acetal or cyclic acetal, protecting one or more alcoholic functions which will be acylated by one or more acylating groups of one kind. The alcohol or the alcohol functions set free after eliminating the protective function will be acylated by the group(s) of a different kind.

(3) The transformation of an alcohol protecting function, directly into an ester function by one or more acylating groups, for example:

(3a) From an epoxy-1,2. By the action of an acid chloride or an acid anhydride according to the reaction scheme:

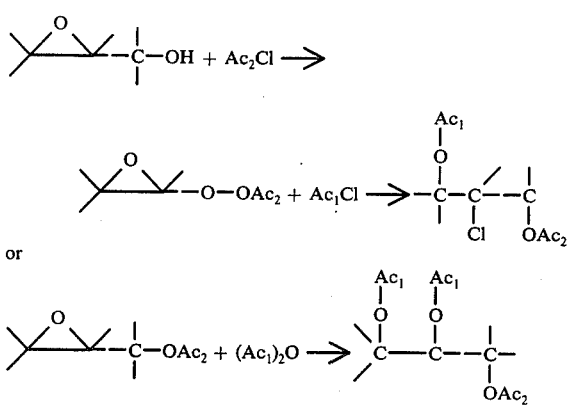

(3b) From a 1,2 epoxyde or by the reaction with a carboxylic function representing an acylating residue.

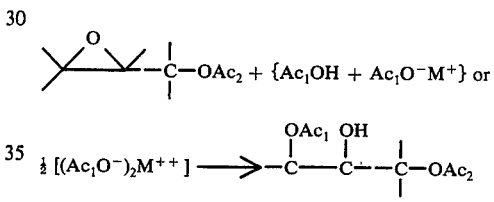

(3c) From a dihalohydrin by reaction with one or more alkaline or alkaline-earth metal carboxylates representing an acylating residue(s):

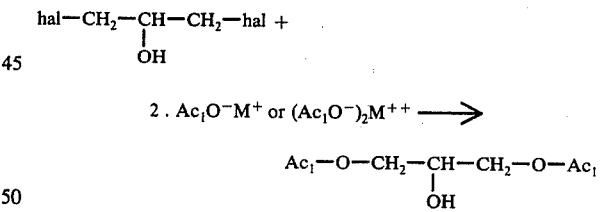

hal being a halogen atom, and M an alkaline or alkaline-earth metal; then the acylation of the free alcohol residue:

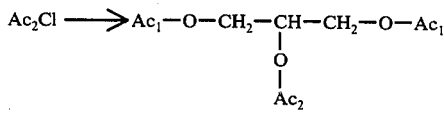

or on the contrary the acylation of the alcohol function of the acylated dihalohydrin with an alkaline or alkaline-earth carboxylate:

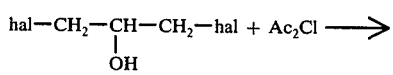

-continued

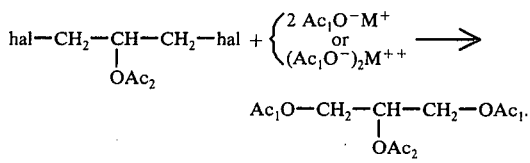

(3d) By the transformation of a cyclic or non-cyclic acetal by an acylating function such as an acid chloride or acid anhydride.

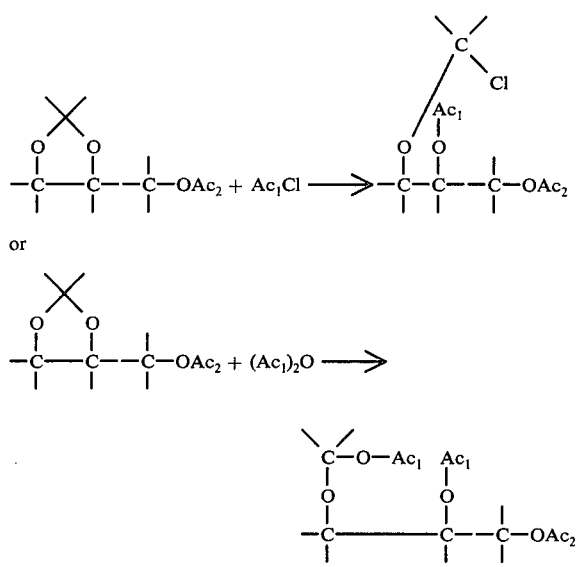

The compounds obtained by the above different methods can be transformed into their pharmaceutically acceptable salts by the action of a suitable acid or base.

The above reactions take place in suitable organic solvents and can be catalysed by catalysts suitable for a specific type of reaction.

The following non-limiting examples illustrate various methods for obtaining the compounds according to the invention.

EXAMPLE 1

Compound (I)

1,2-di-(acetylsalicyl)-3,4,5,6-tetra-(2-p-chlorophenoxy-2-methylpropionyl)-meso-inositol 1(a)  1,2-isopropylidene  3,4,5,6-tetra-(2-p-chlorophenexy-2-methylpropionyl)-meso-inositol 176 g of 1,2-isopropylidene meso-inositol (0.8 mole) are suspended in anhydrous tetrahydrofuran (THF) containing 512 ml of triethylamine (TEA) (3.68 moles) and 200 ml of pyridin. To this solution is added, dropwise, with stirring during 5 hours 857.8 g (3.68 moles) of p-chlorophenoxy methylpropionic acid chloride. After 24 hours, the tetra-ester is separated from the TEA hydrochloride, and it is crystallized in absolute alcohol.

$C_{49}H_{52}Cl_4O_{14}$ (1006,8).

F = 86°–88°

Rf = 0.83 (n-hexane/ethylacetate 2/1 vol.)

IR (characteristic frequencies) 1775, 1745, 1600, 1250, 1240, 1155, 878, 865, 852 cm$^{-1}$.

1(b)  3,4,5,6-tetra-(p-chlorophenoxy-methylpropionyl)-meso-inositol 40.27 g (0.04 mole) of 1(a) and 186 g of ethyleneglycol, as well as 80 mg of p-toluenesulfonic acid are heated at 150° C. for 8 hours under slightly reduced pressure and very strong stirring. The excess of ethyleneglycol and the dioxolane formed are distilled. The residue is extracted with water and ether. The ether phase is evaporated and the product is crystallized from ether.

$C_{46}H_{46}Cl_4O_{14}$ (964.7).

F = 126°–128°

Rf = 0.5 (n-hexane/ethylacetate 2/1 vol.)

1(c)  1,2-di-(acetylsalicyl)-3,4,5,6-tetra-(2-p-chlorophenoxy-2-methylpropionyl)-meso-inositol To a solution of 58 g (0.060 mole) of 1(b) in dry ether containing 16.7 ml of TEA and 50 ml of pyridin, are added 23.8 g (0.120 mole) of the acetylsalicylic acid chloride. After 24 hours, the TEA hydrochloride is separated, and compound (I) is obtained.

$C_{64}H_{60}Cl_4O_{20}$ (1291.0).

$\epsilon_{224\ nm}$ = 56'750 (ethanol 95%)

| Analysis: | Calc. % | Found % |
|---|---|---|
| C | 59.54 | 59.63 |
| H | 4.68 | 4.83 |
| Cl | 10.98 | 11.15 |

Rf = 0.68 (n-hexane/ethylacetate 2/1 vol.)

IR (characteristic frequencies) 1760, 1750–1730, 1610, 1595, 1585 cm$^{-1}$.

EXAMPLES 2

Compound (II)

1,3-di-(2-p-chlorophenoxy-2-methylpropionyloxy)-2-(acetylsalicyloxy)-propane

Method I 2.1.1. 1,3-benzylidene-2-(acetylsalicyloxy)-glycerol

To a solution of 19.8 g (0.11 mole) of 1,3-benzylidene glycerol (b.p. 110°/0.1 Torr.) in dry ether containing 15.3 ml of TEA and 8.9 ml of pyridine, are added dropwise, with stirring, a solution of 21.8 g of acetylsalicylic acid chloride. After 24 hours, the ester is separated from the TEA hydrochloride and product 3 a) is crystallized at −18° in ethylacetate.

$C_{19}H_{18}O_6$ (342.3).

F = 129°–132°

Rf = 0.59 (n-hexane/ethylacetate 2/1 vol.)

IR (characteristic frequencies) 1760, 1710, 1610, 1195 cm$^{-1}$.

2.1.2. 2-(acetylsalicyloxy)-glycerol 2.1.1. is hydrolysed in the presence of palladised charcoal at 10°, after removing the air, and under hydrogen pressure at room temperature.

$C_{12}H_{14}O_6$ (254.2).

Rf = without migration (n-hexane/ethylacetate 2/1 vol.)

IR (characteristic frequencies) 3380, 1765, 1725 cm$^{-1}$.

2.1.3. 1,3-di-(2-p-chlorophenoxy-2-methyl propionyloxy)-2-(acetylsalicyloxy)-propane To a solution in dry ether of 14.9 g (0.0585 mole) of 2.1.2., 16.3 ml of TEA and 9.4 ml of pyridin, is added, dropwise with stirring, a solution in dry ether of 27.3 g (0.117 mole) of p-chlorophenoxy-2-methylpropionic acid chloride. After 15 hours reaction, the product is separated from the TEA hydrochloride and the ether solution is washed with a solution of $CO_3HNa$ in water. After evaporating the solvent, a colourless oil (II) is obtained.

$C_{32}H_{32}Cl_2O_{10}$ (647.5).

| Analysis: | Calc. % | Found % |
|---|---|---|
| C | 59.36 | 59.38 |
| H | 4.98 | 5.02 |
| Cl | 10.95 | 11.11 |

$\epsilon_{226\ nm}$ = 29'730 (ethanol 95%)

Rf = 0.67 (n-hexane/ethylacetate 2/1 vol.)

IR 1760, 1740, 1610, 1595, 1580, 1495, 1475, 1450, 1385, 1365, 1280, 1240, 1200, 1130, 1095, 1080, 1010, 915, 865, 835, 750, 705, 675 $cm^{-1}$.

Compound (II)

1,3-di-(2-p-chlorophenoxy-2-methylpropionyloxy)-2-(acetylsalicyloxy)-propane

Method II 2.2.1. 1-(2-p-chlorophenoxy-2-methylpropionyloxy)-2,3-epoxydo-propane To a solution of 7.4 g (0.1 mole) of 1,2-epoxydo-3-propanol containing 13.93 ml of TEA, is added dropwise 23.3 g (0.1 mole) of 2-p-chlorophenoxy-2-methylpropionic acid chloride in dry ether. After 17 hours, the product is separated from the TEA hydrochloride and the ether solution is washed with an aqueous 5% solution of $CO_3HNa$. The epoxydic ether is distilled, then it is redistilled at 113°–116°/0.09 Torr.

$C_{13}H_{15}Cl\ O_4$ (270.7).

Rf = 0.80 (n-hexane/ethylacetate 2/1 vol.)

IR (characteristic frequencies) 1745, 1600, 1590, 1250, 840, 860 $cm^{-1}$.

2.2.2. 1,3-di-(2-p-chlorophenoxy-2-methylpropionyloxy)-2-propanol

The mixture of 5.4 g of 2.2.1. (0.02 mole) with 4.3 g of p-chlorophenoxy-isobutyric acid (0.02 mole) and 0.47 g of Na p-chlorophenoxy-2-methylpropionate is heated for 2 hours at 120°. After extracting the product with ether, the solution is treated with an aqueous 5% solution of $CO_3HNa$. An oil is obtained which releases at 200°/0.07 Torr. a small fraction of the initial product.

$C_{23}H_{26}Cl_2O_7$ (485.4).

Rf = 0.62 (n-hexane/ethylacetate 2/1 vol.)

IR (characteristic frequencies) 3480, 1740, 1600 et 1590, 1150, 840 et 860 $cm^{-1}$.

2.2.3. 1,3-di-(2-p-chlorophenoxy-2-methylpropionyloxy)-2-acetylsalicyloxy)-propane To a solution of 10.4 g of 2.2.2. in dry ether containing 3 ml of TEA, and 1 ml of pyridin, is added dropwise, with stirring, 4.26 g of acetylsalicylic acid chloride. After 24 hours reaction, the product is separated from the TEA hydrochloride, and the ether solution is washed with an aqueous 5% solution of $CO_3HNa$. An oil (II) is obtained, identical to that obtained under 2.1.3.

Compound (II)

1,3-di-(2-p-chlorophenoxy-2-methylpropionyloxy)-2-(acetylsalicyloxy)-propane

Method III 2.3.1. 1,3-dichloro-2-(salicyloxy)-propane

To a solution of 138 g of salicyclic acid (1 mole) in 645 g of 1,3-chloropropanol, is added 40 ml of concentrated sulfuric acid. After 16 hours at 105° C., the excess of alcohol is distilled at 60°/12 Torr. The residue is dissolved in ether and washed with an aqueous solution of $CO_3NaH$. The ether phase is dried and the solvent removed. The ester is distilled twice at 153°–155°/12 Torr. and at 125°–126°/0.5 Torr. It is crystallized in petroleum ether at −18°.

F = 49°–50° $C_{10}H_{10}Cl_2O_3$ (249.1).

Rf = 0.65 (n-hexane/ethylacetate 2/1 vol.)

IR = 3240, 1685, 1610, 1580, 1480, 1460, 1400, 1395, 1370, 1305, 1295, 1250, 1180, 1150, 1130, 1085, 1035, 880, 780, 760, 710 $cm^{-1}$.

2.3.2. 1,3-di-(2-p-chlorophenoxy-2-methylpropionyloxy)-2-(salicyloxy)-propane

The mixture of 124.5 g of 2.3.1. (0.5 mole) and 236.5 g (1.0 mole) of p-chlorophenoxy-2-methylpropionate of sodium is heated for 10 hours at 180°. It is taken up in ether and filtered. The residue after evaporation of the solvent gives the desired product.

$C_{30}H_{30}Cl_2O_9$ (605.5).

Rf = 0.68 (n-hexane/ethylacetate 2/1 vol.)

IR = 3210, 1735, 1675, 1610, 1590–1580, 1485, 1385, 1360, 1305, 1280, 1250–1245, 1205, 1180–1160, 1130, 1090, 1010, 970, 850-830, 780, 700, 670 $cm^{-1}$.

2.3.3. 1,3-di-(2-p-chlorophenoxy-2-methylpropionyloxy)-2-(acetylsalicyloxy)-propane A solution of 280 g of 2.3.2. in 500 ml of acetic anhydride ($d$=1.08) is refluxed for 1½ hour, then the excess of anhydride is distilled and an oil (II) is obtained, identical to that obtained under 2.1.3.

Compound (II)

1,3-di-(2-p-chlorophenoxy-2-methylpropionyloxy)-2-(acetylsalicycloxy)-propane

Method IV 2.4.1. 1,3-di-(2-p-chlorophenoxy-2-methylpropionyloxy)-2-propanol

A suspension of 118.3 g (0.5 mole) of sodium p-chlorophenoxy-2-methylpropionate in a solution of 60 ml of anhydrous EtOH containing 7.5 g of INa and 64.5 g of 1,3-dichloro-2-propanol (0.5 mole) is refluxed for 90 hours. The solvent is evaporated under reduced pressure and the liquid residue is distilled at 138°–141°/0.07 Torr.

$C_{23}H_{26}Cl_2O_7$ (485.4).

2.4.2. 1,3-di-(2-p-chlorophenoxy-2-methylpropionyloxy)-2-acetylsalicyloxy)-propane 24.2 g (0.05 mole) of 1,3-di-(2-p-chlorophenoxy-2-methyl propionyloxy)-2-propanol is taken up in 300 ml of dry ether containing 0.055 mole of triethylamine, 10.9 g (0.055 mole) of acetylsalicyclic acid chloride and 4 ml of pyridin. After 16 hours reaction with stirring, the organic suspension is filtered and the filtrate washed with a solution of 5% CO₃HNa, then with 2 volumes of H₂O, and dried with SO₄Na₂. The solvent is evaporated under reduced pressured; an oil (II) is obtained identical to that obtained under 2.1.3.

The 1,3-di-(2-p-chlorophenoxy-2-methylpropionyloxy)-2-propanol used as a starting material in step 2.4.2. above can also be prepared as follows: a suspension of 23.7 g (0.1 mole) of p-chlorophenoxy-2-methylpropionate of Na in 14 g (0.11 mole) of 1,3-dichloro-2-propanol is heated in a closed steel cylinder at 155° for 14 hours. After cooling, it is taken up in ether and the soluble fraction is distilled at 138°–141°/0.07 Torr.

Compound (II)

2-(acetylsalicyloxy)-1,3-di-(p-chlorophenoxy-2-methylpropionyloxy)-propane

Method V 2.5.1. 2-acetylsalicyloxy-1,3-dichloropropane

To a solution in THF of 12.9 g (0.1 mole) of 1,3-dichloro-2-propanol, is added 10.1 g (0.1 mole) of TEA, then slowly with stirring, 19.9 g (0.1 mole) of acetylsalicyclic acid chloride. After removing the TEA hydrochloride, acetylsalicyloxy-1,3-dichloropropane is obtained quantitatively, and it crystallizes in petroleum ether.

$C_{12}H_{12}Cl_2O_4$ (291.1) m.p. = 67°–69°.
Rf = 0.58 (ethylacetate/n-hexane 2/1 vol.)
IR = 1750, 1725, 1610, 1580, 1485, 1335, 1295, 1270, 1250, 1200, 1135, 1075, 1010, 915, 820, 760, 700 cm⁻¹.

2.5.2. 2-(acetylsalicyloxy)-1,3-di-(p-chlorophenoxy-2-methylpropionyloxy)-propane To 29.1 g (0.1 mole) of 2.5.1. and 47.3 g of sodium p-chlorophenoxy-2-methylpropionate are admixed. The paste-like mixture is heated at 160° for 5 hours. The product is taken up in ether and the solution is extracted with a solution of 5% CO₃HNa in water, it is washed twice with water and dried with anhydrous SO₄Na₂. The solvent is removed and an oil (II) identical to that obtained under 2.1.3. is obtained quantitatively.

EXAMPLES 3

Compound (III)

3-(acetylsalicyloxy)-1,2-di-(2-p-chlorophenoxy-2-methylpropionyloxy)-propane

Method I 3.1.1. 1-(acetylsalicyloxy)-2,3-epoxydo-propane

To a solution of 44.4 g (0.6 mole) of 1-hydroxy-2,3-epoxydopropane in dry ether, 84 ml of TEA are added, dropwise with stirring, 119.1 g (0.6 mole) 2-acetylsalicyclic acid chloride are also added. After 24 hours, the product is separated from the TEA hydrochloride, and the ether solution is washed with aqueous solution of 5% CO₃NHa. An oily product is isolated.

B.p. 114°–115°/0.02 Torr.
$C_{12}H_{12}O_5$ (263.2).
$\epsilon_{227\ nm}$ = 14'120 (methanol)
Rf = 0.52 (n-hexane/ethylacetate 2/1 vol.)
IR (characteristic frequencies) 1760, 1735, 1610, 1265 cm⁻¹.

3.1.2. 3-(acetylsalicyloxy)-1,2-di(2-p-chlorophenoxy-2-methylpropionyloxy)-propane 23.0 g (0.1 mole) of 3.1.1. are mixed with 41.1 g (0.1 mole) of p-chlorophenoxy-2-methylpropionic acid anhydride, at a temperature of 100°. The mixture becomes homogeneous, the temperature of the mixture is then brought to 120° for 1½ hour. The product is extracted with ether, washed with an aqueous solution of 5% CO₃HNa, then decolored with active charcoal. A colourless oil (III) is obtained.

| $C_{32}H_{32}Cl_2O_{10}$ (647.5) Analysis: | Calc. % | Found % |
|---|---|---|
| C | 59.35 | 59.32 |
| H | 4.94 | 5.22 |
| Cl | 10.97 | 11.11 |

$\epsilon_{226\ nm}$ = 30'900 (ethanol 95%)
Rf = 0.67 (n-hexane/ethylacetate 2/1 vol.)
Cc = homogeneous peak (carbowax 4%, temperature 152°, N₂ 30 ml/mn
IR (characteristic frequencies) 1760–1730, 1610, 1600 and 1595, 840 and 860 cm⁻¹.

Note:

For the 3.1.2. reaction, the temperature can be between 60° and 220°; in the presence of a Lewis acid such as BF (introduced in the form of BF₃O(C₂H₅) or BF₃(C₅H₆N), the reaction can be carried out at ordinary temperature. The reaction can also be effected in a solvent inert to the anhydride and the epoxyde function.

Compound (III)

1,2-di-(2-p-chlorophenoxy-2-methylpropionyloxy)-3-acetylsalicyloxy)-propane

Method II 3.2.1. 3-chloro-1,2-di(p-chlorophenoxy-2-methylpropionyloxy)-propane 41.1 g (0.1 mole) of the p-chlorophenoxy-2-methylpropionic acid anhydride are added to 9.25 g (0.1 mole) of epichlorhydrin. It is heated to 130°, then the excess of unreacted anhydride is removed by hydrolysis with CO₃HNa. An oil is obtained.

$C_{23}H_{25}Cl_3O_6$ (503.8).
IR = 1745, 1592, 1490, 1480, 1390, 1370, 1280, 1240, 1150, 1130, 1100, 1015, 970, 855, 845, 770, 725, 710, 680 cm⁻¹.

3.2.2. 1,2-di-(2-p-chlorophenoxy-2-methylpropionyloxy)-3-(salicyloxy)-propane 25 g (0.05 mole) of 3.2.1. are mixed with 12 g (0.075 mole) of sodium salicylate and heated to 180° for 16 h. The sodium chloride is removed by desalting the product in ether. An oil is obtained.
$C_{30}H_{30}Cl_2O_9$ (605.5).
IR = 1740, 1680, 1590, 1575, 1485, 1380, 1360, 1300, 1240, 1180, 1160, 1120, 1090, 1010, 965, 850, 825, 760, 695, 680 cm⁻¹.

3.2.3. 1,2-di-(2-p-chlorophenoxy-2-methylpropionyloxy)-3-acetylsalicyloxy)-propane 28 g (0.04 mole) of 3.2.2. are dissolved in 50 ml of acetic anhydride, and heated to 105°. The excess of reagent is removed by washing the ether solution with an aqueous solution of 5% CO₃HNa. The organic phase is dried with SO₄Na₂. An oil (III) is obtained identical to that obtained under 3.1.2.

EXAMPLE 4

Compound (IV)

1-(acetylsalicyloxy)-3-(2-p-chlorophenoxy-2-methyl-propionyloxy)-2-acetoxy-propane 4.1. 1-(acetylsalicyloxy)-3-(2-p-chlorophenoxy-2-methylpropionyloxy)-2-propanol A solution of 21.4 g (0.1 mole) of p-chlorophenoxy-2-methylpropionic acid and 23.6 g (0.1 mole) of 1-(acetylsalicyloxy)-2,3-epoxydo-propane in 100 ml of dimethylformamide is heated to 80° for 18 hours. After distilling the solvent, the residue is washed with $CO_3HNa$ from an ether solution. 26 g of an oil are obtained.
$C_{22}H_{23}Cl\ O_8$ (450.9).
Rf = 0.12 (ethylacetate/hexane 1/2 vol.)
IR = 3500, 1770, 1735–1740, 1610, 1595, 1580, 1490, 1370, 1290, 1260–1240, 1200, 1140, 1080, 1010, 830, 750, 705, 570 cm$^{-1}$.

4.2. 1-(acetylsalicyloxy)-3-(2-p-chlorophenoxy-2-methylpropionyloxy)-2-acetoxy-propane 9 g of 1-(2-acetylsalicyloxy)-3-(2-p-chlorophenoxy-2-methylpropionyloxy)-2-propanol (0.02 mole) are dissolved in 5 ml of acetic acid containing 5 ml of acetic anhydride. After 4 hours at ordinary temperature, the excess of reagent and the solvent are removed. It is taken up in ether and the solution is washed with a solution of 5% $CO_3HNa$ in water. An oil (IV) is obtained.

| $C_{24}H_{25}Cl\ O_9$ (492.9) Analysis: | Calc. % | Found % |
|---|---|---|
| C | 58.48 | 58.39 |
| H | 5.11 | 5.19 |
| Cl | 7.19 | 7.16 |

$\epsilon_{227\ nm}$ = 18'700 (ethanol 95%)
Rf = 0.38 (ethylacetate/hexane 1/2 vol.)
IR = 1770, 1740, 1600, 1595, 1580, 1490, 1270, 1230, 1195, 1130, 1080, 1010, 960, 910, 815, 750, 700, 680 cm$^{-1}$.

EXAMPLE 5

Compound (V)

1-(acetylsalicyloxy)-3-(2-p-chlorophenoxy-2-methylpropionyloxy)-2-sulfopropanol

Sodium salt 9 g (0.02 mole) of 1-(acetylsalicyloxy)-3-(2-p-chlorophenoxy-2-methylpropionyloxy)-2-propanol 4.1. are dissolved in 100 ml. of acetonitrile to which is added 6.04 g (0.038 mole) of pyridine-sulfuric anhydride ($C_5H_5NSO_3$). After 12 hours stirring at ordinary temperature, the excess of ether is filtered. It is neutralised with $CO_3HNa$, and 5.4 g of a solid (V) are obtained.

| $C_{22}H_{22}Cl\ O_{11}\ SNa$ (552.9) Analysis: | Calc. % | Found % |
|---|---|---|
| C | 47.79 | 47.57 |
| H | 4.01 | 4.21 |
| S | 5.80 | 5.85 |

$\epsilon_{226\ nm}$ = 19'175 (ethanol 95%)
Rf = 0.7 (n-butanol/acetic acid/$H_2O$ 10/2/3, vol.)

IR = 1770, 1750–1725, 1605, 1595, 1580, 1485, 1280, 1240, 1200, 1130, 1090, 1040, 1010, 940, 830, 750, 700 cm$^{-1}$.

EXAMPLES 6

Compound (VI)

1-(acetylsalicyloxy)-2-(2-p-chlorophenoxy-2-methylpropionyloxy)-ethane

Method I 6.1.1. 1-(2-p-chlorophenoxy-2-methylpropionyloxy)-2-chloro-ethane 107.3 g (0.5 mole) of p-chlorophenoxy-2-methylpropionic acid are dissolved in 241.5 g (3 moles) of 2-chloroethanol. The solution is saturated with HCl gas. The excess of solvent is distilled under 11 Torr. The ester is distilled under 0.02 Torr, at a temperature of 97°–98°.
$C_{12}H_{14}Cl_2O_3$ (277.1).
Rf = 0.88 (ethylacetate/n-hexane 1/2 vol.)
IR = 1740, 1590, 1580, 1485, 1385, 1280, 1240, 1180, 1140, 1090, 1010, 970, 825, 670 cm$^{-1}$.

6.1.2. 1-(2-p-chlorophenoxy-2-methylpropionyloxy)-2-(salicyloxy)-ethane 50 g (0.18 mole) of 1-(2-p-chlorophenoxy-2-methylpropionyloxy)-2-chloro-ethane are mixed with 43.3 g (0.27 mole) of sodium salicylate. The mixture is heated to 195° for 8 hours. The products are taken up in ether, and NaCl is removed by filtration. The diester crystallizes quantitatively from the ether solution.
m.p. = 43°–45°
$C_{19}H_{19}Cl\ O_6$ (378.8).
Rf = 0.7 (ethylacetate/n-hexane 1/2 vol.)
IR = 3220, 1720, 1675, 1605, 1590, 1575, 1480, 1330, 1290, 1240, 1180, 1150, 1090, 1040, 980, 820, 760, 720, 660 cm$^{-1}$.

6.1.3. 1-(2-p-chlorophenoxy-2-methylpropionyloxy)-2-(acetylsalicyloxy)-ethane

To a solution of 68 g of 1-(2-p-chlorophenoxy-2-methylpropionyloxy)-2-(salicyloxy)-ethane in 30 ml of pyridine, 34 ml of acetic anhydride are added. After 2½ hours, the excess of reagent is removed, then the product is heated to 150°, under a vacuum of 0.05 Torr. An oil is obtained which crystallizes spontaneously at ordinary temperature (VI).

| $C_{21}H_{21}Cl\ O_7$ (420.9) Analysis: | Calc. % | Found % |
|---|---|---|
| C | 59.93 | 60.03 |
| H | 5.03 | 5.12 |

$\epsilon_{226\ nm}$ = 19'950 (ethanol 95%)
m.p. = 48°–50°
Rf = 0.55 (ethylacetate/n-hexane ½ vol.)
IR = 1760, 1710–1720, 1600, 1590, 1570, 1485, 1265, 1195, 1150, 1080, 1050–1040, 1000, 910, 820, 750, 700, 665 cm$^{-1}$.

Compound (VI)

1-(acetylsalicyloxy)-2-(2-p-chlorophenoxy-2-methylpropionyloxy)-ethanol

Method II 6.2.1. 1-(2-p-chlorophenoxy-2-methylpropionyloxy)-2-ethanol 23.6 g (0.1 mole) of 2-p-chlorophenoxy-2-methyl propionate of Na are introduced into 18 g (0.22 mole) of chloroethane. It is refluxed for 2 hours at 160°, then the excess of solvent is removed. The residue is taken up with ether and the alcohol is distilled. B.p. = 110°–117°/0.02 Torr.

Rf = 0.35 (ethylacetate/n-hexane ½ vol.)

IR = 3440, 1730, 1590, 1580, 1485, 1385, 1360, 1280, 1240, 1180, 1140, 1090, 1010, 970, 890, 850–830, 670 cm$^{-1}$.

6.2.2. 1-(2-p-chlorophenoxy-2-methylpropionyloxy)-2-(acetylsalicyloxy)-ethane

To a solution of 5.17 g (0.02 mole) of 6.2.1. in dry ether, 2.8 ml (0.02 mole) of triethylamine are added and, dropwise with stirring, 4.05 g (0.02 mole) of acetylsalicylic acid chloride are introduced. The hydrochloride of triethylamine formed is filtered, and the ether solution is extracted with an aqueous solution of 5% CO$_3$HNa. The solution in which the product crystallizes spontaneously is dried. It is recrystallized in petroleum ether, and a product (VI) identical to that prepared under 6.1.3. is obtained.

Compound (VI)

1-(acetylsalicyloxy)-2-(2-p-chlorophenoxy-2-methyl-propionyloxy)-ethane

Method III 6.3.1. 1-salicyloxy-2-chloro-ethane

A solution of 13.8 g (0.1 mole) of salicylic acid in 48.3 g (0.6 mole) of 2-chloro-ethanol in the presence of 4 ml of sulfuric acid is heated to 110° for 2 hours. After removing the excess of 2-chloro-ethanol, the ether solution of the product is extracted with an aqueous solution of 5% CO$_3$HNa. The ether is removed and the product is distilled. B.p.: 128°–129°/11 Torr.

C$_9$H$_9$Cl O$_3$ (200.6).

Rf = 0.80 (ethylacetate/n-hexane 1/2 vol.)

6.3.2. 1-salicyloxy-2-(2-p-chlorophenoxy-2-methylpropionyloxy)-ethane

A mixture of 2 g (0.91 mole) of 6.3.1. and 3.55 g (0.015 mole) of Na p-chlorophenoxy-2-methylpropionate is heated for 4 hours at 180°. It is taken up in ether, filtered, and the product is crystallized; it is identical to 6.1.2.

6.3.3. 1-(acetylsalicyloxy)-2-(2-p-chlorophenoxy-2-methylpropionyloxy)-ethane

From the 1-salicyloxy-2-(2-p-chlorophenoxy-2-methylpropionyloxy)-ethane obtained under 6.3.2., product (VI) is prepared, as under 6.1.3.

Compound (VI)

1-(acetylsalicyloxy)-2-(2-p-chlorophenoxy-2-methyl-propionyloxy)-ethane

Method IV 6.4.1. 1-(2-p-chlorophenoxy-2-methylpropionyloxy)-2-ethane

To a solution of 6.2 g (0.1 mole) of ethyleneglycol in THF, 13.93 ml (0.1 mole) of triethylamine, and dropwise 23.3 g (0.1 mole) of p-chlorophenoxy-2-methylpropionic acid chloride in THF are added. The triethylamine hydrochloride precipitated is filtered, the ether solution is washed with an aqueous solution of 5% CO$_3$HNa. The solvent is removed, and the product is distilled at 0.02 Torr. The product is identical to that obtained under 6.2.1.; from the thus obtained 1-(2-p-chlorophenoxy-2-methylpropionyloxy)-2-ethanol, product (VI) is prepared as under 6.2.2.

Compound (VI)

1-(acetylsalicyloxy)-2-(2-p-chlorophenoxy-2-methyl-propionyloxy)-ethane

Method V 6.5.1. 1-(2-p-chlorophenoxy-2-methylpropionyloxy)-2-chloro-ethane

To a solution of 80.5 g of chloro-ethanol (1 mole) in THF containing 101 g (1 mole) of triethylamine are added, dropwise with stirring, 233 g (1 mole) of p-chlorophenoxy-2-methylpropionic acid chloride. The triethylamine hydrochloride is filtered, and the ester formed is distilled; it is identical to that obtained under 6.1.1.; the synthesis of (VI) is continued as under 6.1.2., and then 6.1.3.

PHARMACOLOGICAL PROPERTIES (A) Acute toxicity

The acute toxicity of compounds I to VI was determined on the male rat (Table I).

| Product | Administration means | LD$_{50}$ | g/kg |
|---|---|---|---|
| I | p.o. | > 5 | g/kg |
| II | p.o. | > 7.5 | g/kg |
| III | p.o. | > 6.2 | g/kg |
| IV | p.o. | > 5 | g/kg |
| V | p.o. | > 5 | g/kg |
| VI | p.o. | > 6 | g/kg |

All these derivatives are therefore much less toxic than the clofibrate (LD$_{50}$:1.2 g/kg) and acetylsalicylic acid (LD$_{50}$:1.75 g/kg).

(B) Pharmacocinetics

All the compounds this patent is directed to release clofibric acid and acetylsalicylic acid in the blood. The metabolites were determined by gas chromatography after transformation to silane derivatives. Two peaks are observed, one representing the sum of salicylated derivatives and the other clofibric acid. In Table II, the maximum plasma levels attained in the rat after a single administration are given.

TABLE II

| Product | Dose p.o. mg/kg | Max.plasma levels µg/ml salicyl derivatives | clofibric acid | After x hours |
|---|---|---|---|---|
| Test: clofibrate + acetylsal. ac. | 300 + 100 | 180 | 280 | 1 |
| Compound I | 400 | 30 | 45 | 16 |
| " II | 400 | 40 | 60 | 16 |
| " III | 400 | 45 | 58 | 16 |
| " IV | 400 | 150 | 115 | 8 |
| " V | 400 | 60 | 175 | 3 |
| " VI | 400 | 150 | 200 | 8 |

It is seen that the release of two active metabolites can be influenced by modifying the steric hindrance of the compounds in question, indeed, when the steric hindrance is increased, the metabolisation thereof is slowed down.

(C) Hypocholesterolemiating and hypolipemiating activity

Groups of 10 normolipemiating rats were treated for 10 days, by gastric probe, with the equivalent of 75 mg/kg of clofibrate, administered every 12 hours. After 10 days, 12 hours after the last administration, they were sacrificed and the cholesterol and triglycerides analysed (Table III).

TABLE III

| Product | Triglycerides mm mole/l. | Decrease % | Cholesterol mg/100 ml | Decrease % |
| --- | --- | --- | --- | --- |
| Test: without treatment | 1.13 | | 90.79 | |
| Test: clofibrate | 0.83 | 27 | 65.24 | 28 |
| Compound I | 0.96 | 15 | 78.25 | 14 |
| Compound II | 0.92 | 19 | 73.90 | 19 |
| Compound III | 0.91 | 19 | 75.63 | 17 |
| Compound IV | 0.97 | 14 | 72.12 | 21 |
| Compound V | 0.89 | 21 | 68.38 | 25 |
| Compound VI | 0.83 | 27 | 67.34 | 26 |

(D) Anti-aggregating and anti-adhesive activity

The anti-aggregating and anti-adhesive activity of compounds I to VI was tested ex vivo on the rabbit after an administration equivalent to 50 mg/kg of acetylsalicylic acid. All the compounds possess both anti-aggragating and anti-adhesive activity (ADP, collagen) identical to that of the blanks (50 mg/kg of acetylsalicylic acid). The blood was taken, under narcosis, 24 hours after administration of the dose (intubation).

THERAPEUTICAL APPLICATIONS

Compounds I-VI are intended for the treatment of mixed hypercholesterolamiae and hyperlipidemiae, hyperaggragability of the platelets, as well as atherosclerous effects connected with such disorders. The compounds are administered orally in one or several doses daily at a dosage of 0.30 g to 4 g per day according to the gravity of the illness and the results of laboratory examinations. The compounds are given alone or with pharmaceutically acceptable vehicles, e.g. in the form of hard or soft capsules, plain or coated tablets, granulates or syrups.

We claim:

1. Therapeutically active compounds of the general formula:

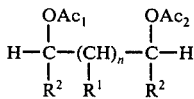

wherein $n$ is 0, 1, 2, 3 or 4;

$Ac_1$ is the 2-p-chloro-phenoxy-2-methylpropionyl or clofibril group of the formula:

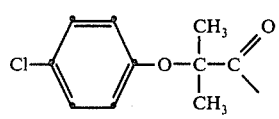

$Ac_2$ is the 2-acetylsalicyl group of the formula:

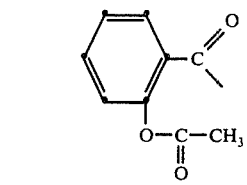

$R_1$ is hydrogen, $-OAc_1$, $-OAc_2$ or $-OSO_3H$, and $R_2$ is hydrogen or both $R^2$ together form a single bond.

2. A compound according to claim 1, of formula:

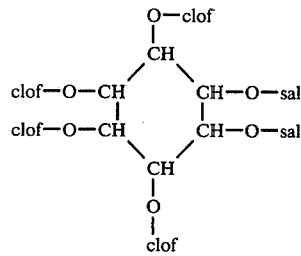

the inosite being of meso- form and clof signifying the clofibril residue and sal is the 2-acetylsalicyl residue.

3. A compound according to claim 1, of formula:

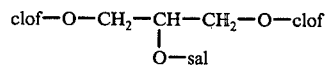

wherein clof indicates the clofibril residue and sal the 2-acetylsalicyl residue (Example 2).

4. A compound according to claim 1, of formula:

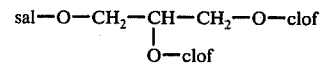

wherein clof indicates the clofibril residue and sal indicates the 2-acetylsalicyl residue (Example 3).

5. A compound according to claim 1, of formula:

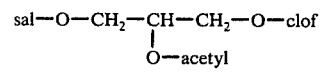

wherein clof indicates the clofibril residue and sal indicates the 2-acetylsalicyl residue (Example 4).

6. A compound according to claim 1, of formula:

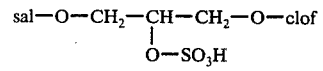

wherein clof indicates the clofibril residue and sal indicates the 2-acetylsalicyl residue (Example 5).

7. A compound according to claim 1, of formula:

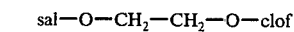

wherein clof indicates the clofibril residue and sal indicates the acetylsalicyl residue (Example 6).

* * * * *

UNITED STATES PATENT AND TRADEMARK OFFICE
CERTIFICATE OF CORRECTION

PATENT NO. : 4,118,583
DATED : October 3, 1978
INVENTOR(S) : Pierre Baudet, Jean-Paul Ricard and Adrian Schulthes:

It is certified that error appears in the above-identified patent and that said Letters Patent are hereby corrected as shown below:

In the claims, claim 3, line 1, the words "according to claim 1" should be cancelled.

*Signed and Sealed this*

*Thirty-first* Day of *July 1979*

[SEAL]

Attest:

LUTRELLE F. PARKER
*Attesting Officer*   *Acting Commissioner of Patents and Trademarks*